United States Patent

Colson et al.

[11] Patent Number: 5,872,290
[45] Date of Patent: Feb. 16, 1999

[54] PREPARATION OF ACID CHLORIDES

[75] Inventors: James G. Colson; Ramesh Krishnamurti, both of Williamsville; Rose Adinolfe, Newfane, all of N.Y.

[73] Assignee: Occidental Chemical Corporation, Niagara Falls, N.Y.

[21] Appl. No.: 965,817

[22] Filed: Nov. 7, 1997

[51] Int. Cl.[6] ................................................. C07C 51/58
[52] U.S. Cl. ........................................................... 562/863
[58] Field of Search ............................................. 562/863

[56] References Cited

U.S. PATENT DOCUMENTS 4,388,251  6/1983  Clifford .

FOREIGN PATENT DOCUMENTS 420346   1/1911  France .
1510275  1/1968  France .
2754670  6/1979  Germany .
1152637  7/1986  Japan .
56739    3/1994  Japan .

OTHER PUBLICATIONS

Advanced Organic Chemistry by Jerry March, Fourth Edition p. 697 (1992).
An Article by Franz Effenberger et al., Titled Enzyme Catalyzed Addition of Hydrocyanic Acid to Substituted Pivaldehydes—A Novel Synthesis of (R)–"Pantolactone" in Tetrahedron: Asymmetry, vol. 6, No. 1—pp. 271 to 282 (1995).

Organic Synthesis, Collective vol. I 2nd Edition (1958), pp. 155 to 156 by H. T. Clarke et al.

Primary Examiner—Paul J. Killos
Attorney, Agent, or Firm—Richard D. Fuerle

[57] ABSTRACT

Disclosed is a method of making an acid chloride having the general formula

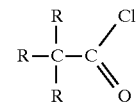

where each R contains no unsaturated groups and is preferably independently selected from aliphatic from $C_1$ to $C_7$ and aryl from $C_6$ to $C_{15}$. A solution is formed in an inert solvent of an aldehyde having the general formula

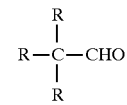

and chlorine gas is sparged into said solution. The reaction between the aldehyde and the chlorine gas to produce the acid chloride is performed in the absence of a catalyst, an initiator, and ultraviolet light. A chlorinated acid chloride can be prepared from the acid chloride by reacting it with additional chlorine in the presence of a chlorine free radical generator.

20 Claims, No Drawings

PREPARATION OF ACID CHLORIDES

BACKGROUND OF THE INVENTION

This invention relates to a method of making an acid chloride from an aldehyde. In particular, it relates to reacting pivaldehyde with chlorine gas to make pivaloyl chloride, which can then be chlorinated to produce cloropivaloyl chloride.

Chloropivaloyl chloride (CPC) is a commercially important raw material used in making herbicides. U.S. Pat. Nos. 5,312,982 and 4,770,821) teach that CPC can be prepared by chlorinating pivaloyl chloride (PC). Pivaloyl chloride is prepared from pivalic acid by reaction with either phosgene or thionyl chloride, both of which are relatively expensive.

SUMMARY OF THE INVENTION

We have discovered that CPC and other chlorinated acid chlorides can be made in a new two step process. In the first step, an aldehyde is reacted with chlorine gas to produce an acid chloride. In the second step, the acid chloride is reacted with chlorine gas in the presence of a chlorine free radical generator to produce a chlorinated acid chloride.

The aldehyde and chlorine gas starting materials are relatively inexpensive and the process does not produce significant amounts of highly chlorinated byproducts.

DESCRIPTION OF THE PREFERRED EMBODIMENTS

The process of this invention begins with an aldehyde having the general formula:

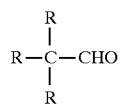

where each R is independently selected from groups containing 1 to 20 carbon atoms. To prevent reaction with the chlorine, the R groups contain no unsaturation. Preferably, each R is independently selected from aliphatic from $C_1$ to $C_7$ and aryl from $C_6$ to $C_{15}$, and most preferably each R is independently selected from alkyl from $C_1$ to $C_4$ and aryl from $C_6$ to $C_{12}$. As the general formula indicates, the aldehyde does not have an alpha hydrogen, so alpha chlorination is avoided. Examples of aldehydes that can be used include pivaldehyde (PA), also known as trimethyl acetaldehyde, triphenyl acetaldehyde, chlorodiphenyl acetaldehyde, dichlorophenyl acetaldehyde, trichloro acetaldehyde, and tris(trifluoromethyl) acetaldehyde; the preferred aldehyde is PA due to its commercial importance. Many of these aldehydes are commercially available and others can be prepared by known processes.

In the first step of the process of this invention, the aldehyde is reacted with chlorine gas to produce the corresponding acid chloride:

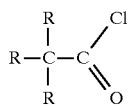

To avoid the production of unwanted byproducts such as the t-alkyl chloride, an inert solvent is used in this first reaction. The aldehyde is dissolved in the solvent and chlorine gas is sparged into the resulting solution. The solvent should be a liquid between about 80° C. and about 250° C. In general, the choice of a solvent depends upon the boiling point of the acyl chloride to be prepared, the solvent being selected so that it can be easilty separated from the acyl chloride by distillation. Chlorinated benzenes, such as mono-, di-, and tri-chlorobenzenes, and particularly o-dichlorobenzene (ODCB), are the preferred solvents. Other aromatic solvents that lack active hydrogens and also lack ether linkages, such as benzotrifluoride, p-chlorobenzotrifluoride, and dichlorobenzotrifluoride can also be used.

No initiator, catalyst, or ultraviolet light (UV), is used in this reaction as they not only add to the cost of the reaction, but also reduce the yield and selectivity. Since the reaction proceeds in the absence of light, the process can be carried out industrially in glass-lined steel reactors.

The reaction is complete when chlorine breakthrough is observed. The reaction can be followed by gas chromatography (GC).

The acid chloride made in the first reaction can be can be used in the second reaction without isolating it, or, if desired, it can be isolated by, for example, distillation, before being used in the second reaction. In the second reaction, the acid chloride is chlorinated with chlorine gas to produce a chlorinated acid chloride. If more than one site is available for replacement of a hydrogen by a chlorine on the acid chloride, a mixture of products is likely to be produced and separation of the products in the mixture by, for example, distillation, may be necessary. Since chlorine will preferentially replace a methylene hydrogen over methyl hydrogens, greater specificity can be achieved if the acid chloride has only a single methylene hydrogen. That is, since specificity is desirable, the acid chloride preferably has a general formula such as:

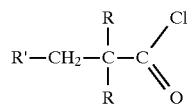

where R is as hereinbefore defined but does not contain a methylene hydrogen and R' is hydrogen, halogen, phenyl, methyl, or perfluoroalkyl from $C_1$ to $C_4$.

The second reaction is performed in the liquid phase at a temperature of about 60° to about 100° C. This reaction should be carried out using less than a stoichiometric amount of chlorine gas. A chlorine free radical initiator, such as UV light, azobis(isobutyronitrile) (AIBN), or a peroxide reagent such as a dialkyl peroxide, diacyl peroxide, dialkylperoxydicarbonate, or alkylperester, is used in this reaction. If an acid chloride having the above formula is used in the second chlorination reaction, the product will be a chlorinated acid chloride having the general formula:

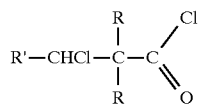

If no solvent is present, unreacted acid chloride can be recycled. If the acid chloride from the first reaction is not isolated and a solvent is present, the solvent can be removed by distillation. The final chlorinated acid chloride product can be purified by distillation.

The following examples further illustrate this invention.

EXAMPLE 1

In the following experiments an aldehyde was reacted with chlorine gas in a three-necked flask under various conditions in the absence of an initiator or a catalyst, with and without ambient light. The following table gives the conditions and a GC analysis of the product mixture.

| Run # | Aldehyde | PA wt %/ solvent | Initiator Conc (ppm) | T(°C.) | Aldehyde | Acid Chloride | t-BuCl | Other* | Light Source |
|---|---|---|---|---|---|---|---|---|---|
| 1 | PA | 20 wt %/ ODCB | AIBN/426 | 65–70 | 15 | 50 | 12 | 22 | Ambient |
| 2 | PA | 20 wt %/ ODCB | AIBN/426 | 30–35 | 12 | 68 | 5 | 14 | Ambient |
| 3 | PA | 20 wt %/ ODCB | Not used | 30–35 | <1 | 85 | 2 | 10 | Ambient |
| 4 | PA | Neat | Not used | 35–45 | 5 | 25 | 44 | 24 | Ambient |
| 5 | CPA | 20 wt %/ ODCB | Not used | 40–50 | <1 | 94 | — | 5 | Ambient |
| 6 | PA | 20 wt %/ ODCB | Not used | 30–40 | 1 | 60 | 2 | 38 | None |

*Not fully characterized

The experiments show that the presence of the initiator reduced the yield of the acid chloride product (Run 2 vs. Run 3), that the yield was higher at the lower reaction temperature (Run 1 vs. Run 2), and that the solvent significantly enhanced the yield (Run 4). Run 6 shows that the chlorination reaction proceeds even in the dark.

We claim:

1. A method of making an acid chloride having the general formula

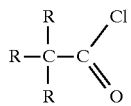

comprising (A) forming a solution in an inert solvent of an aldehyde having the general formula

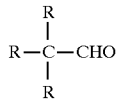

where each R is a group containing 1 to 20 carbon atoms and no unsaturated groups; and (B) sparging chlorine gas into said solution, where the reaction between said aldehyde and said chlorine gas to produce said acid chloride is performed in the absence of a catalyst, an initiator, and ultraviolet light.

2. A method according to claim 1 wherein each R is independently selected from aliphatic from $C_1$ to $C_7$ and aryl from $C_6$ to $C_{15}$.

3. A method according to claim 1 wherein one R group contains a single methylene group and the remaining R groups contain no methylene groups.

4. A method according to claim 1 wherein said aldehyde has the R

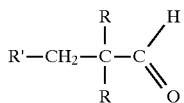

general formula where R' is hydrogen, halogen, phenyl, methyl, or perfluoroalkyl.

5. A method according to claim 1 wherein said aldehyde is pivaldehyde.

6. A method according to claim 1 wherein said aldehyde is chloropivaldehyde.

7. A method according to claim 1 wherein said inert solvent is a chlorinated benzene.

8. A method of making a chlorinated acid chloride comprising (A) forming a solution in an inert solvent of an aldehyde having the general formula

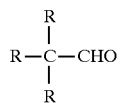

where each R contains no unsaturated groups and is independently selected from aliphatic from $C_1$ to $C_7$ and aryl from $C_6$ to $C_{15}$;

(B) sparging chlorine gas into said solution, whereby said aldehyde and said chlorine gas react to produce an acid chloride and where that reaction is performed in the absence of a catalyst, an initiator, and ultraviolet light; and (C) reacting said acid chloride with chlorine gas in the presence of a chlorine free radical generator to produce said chlorinated acid chloride.

9. A method according to claim 8 wherein each R is independently selected from aliphatic from $C_1$ to $C_4$ and aryl from $C_6$ to $C_{12}$.

10. A method according to claim 9 wherein said aldehyde has the general formula

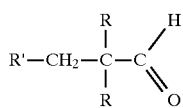

where R' is hydrogen, halogen, phenyl, methyl or perfluoroalkyl from $C_1$ to $C_4$.

11. A method according to claim 10 wherein said aldehyde is pivaldehyde.

12. A method according to claim 8 wherein said inert solvent is a chlorinated benzene.

13. A method according to claim 8 wherein the acid chloride formed in step (B) is isolated before being used in step (C).

14. A method according to claim 8 wherein the acid chloride formed in step (B) is not isolated before being used in step (C).

15. A method of making chloropivaloyl chloride comprising (A) forming a solution of pivaldehyde in an inert solvent;

(B) sparging chlorine gas into said solution, whereby said pivaldehyde and said chlorine gas react to produce pivaloyl chloride and that reaction is performed in the absence of a catalyst, an initiator, and ultraviolet light; and (C) reacting said pivaloyl chloride with chlorine gas in the presence of a chlorine free radical generator to produce said chloropivaloyl chloride.

16. A method according to claim 15 wherein said chlorine free radical generator is UV light.

17. A method according to claim 15 wherein said chlorine free radical generator is an organic peroxide reagent.

18. A method according to claim 15 wherein said inert solvent is o-dichlorobenzene.

19. A method according to claim 15 wherein the acid chloride formed in step (B) is isolated before being used in step (C).

20. A method according to claim 15 wherein the acid chloride formed in step (B) is not isolated before being used in step (C).

* * * * *